(12) United States Patent
Bernstein

(10) Patent No.: US 7,371,367 B2
(45) Date of Patent: May 13, 2008

(54) METHOD OF TREATING INFLAMMATORY ACNE VULGARIS AND ROSACEA WITH CARBAMIDE PEROXIDE

(75) Inventor: Joel E. Bernstein, Deerfield, IL (US)

(73) Assignee: Exopharma, Inc., Vernon Hills, IL (US)

( * ) Notice: Subject to any disclaimer, the term of this patent is extended or adjusted under 35 U.S.C. 154(b) by 379 days.

(21) Appl. No.: 10/897,939

(22) Filed: Jul. 23, 2004

(65) Prior Publication Data

US 2006/0020025 A1    Jan. 26, 2006

(51) Int. Cl.
  *A61K 8/81*  (2006.01)
  *A61K 8/73*  (2006.01)
  *A61K 8/37*  (2006.01)

(52) U.S. Cl. .............. 424/70.13; 424/70.16; 424/70.31

(58) Field of Classification Search ......... 514/24, 514/554, 588; 424/70.13, 70.16, 70.31
  See application file for complete search history.

(56) References Cited

U.S. PATENT DOCUMENTS 4,607,101 A * 8/1986 Bernstein ............... 514/24
2004/0220264 A1 * 11/2004 Yu et al. ............... 514/554

* cited by examiner

*Primary Examiner*—Ardin Marschel
*Assistant Examiner*—Zohreh Vakili
(74) *Attorney, Agent, or Firm*—Barnes & Thornburg, LLP; Alice O. Martin

(57) ABSTRACT

A method of treating inflammatory acne vulgaris or inflammatory acne rosacea comprises the topical application of a formulation incorporating carbamide peroxide in a pharmaceutically acceptable vehicle. Inflammatory acneform lesions that can be successfully treat with the inventive method include erythematous papules, pustules, nodules, and cysts. Suitable pharmaceutical vehicles for the topical application of carbamide peroxide include creams, gels, lotions, solutions, suspensions, and ointments.

3 Claims, No Drawings

METHOD OF TREATING INFLAMMATORY ACNE VULGARIS AND ROSACEA WITH CARBAMIDE PEROXIDE

BACKGROUND OF THE INVENTION

Acne vulgaris is a disease of the pilosebaceous glands characterized by an unsightly eruption of the skin of the face, neck, back and chest. Acne vulgaris is a common affliction of the adolescent and affects a small but significant percentage of the adult population. Acne vulgaris lesions are of four basic types: comedones (blackheads or whiteheads,) papules, pustules, and cysts (or nodules). Various topical agents used in the treatment of acne vulgaris include sulfur, sulfur compounds, resorcinol, salicylic acid, benzoyl peroxide, various retinoids including tretinoin, tazarotine and adopalene, and topical antibiotics. Acne vulgaris involvement results in unsightly lesions, particularly on the face, and in some cases results in severe scarring.

Acne rosacea, commonly called simply rosacea, is an inflammatory disorder of the skin that, despite its name, seems to bear no relationship to acne vulgaris. In contrast to acne vulgaris, rosacea occurs predominantly in middle-aged adults and is virtually never observed in adolescents or young adults. Rosacea is characterized by inflammatory lesions of the skin that resemble acne vulgaris papules and pustules ("acneform" lesions) and a disorder of the superficial cutaneous vasculature resulting in erythema, accentuated flushing and telangiectasia. Comedones, a hallmark of acne vulgaris, do not occur as part of the rosacea "complex." Rosacea is treated with a variety of topical therapies including sodium sulfacetamide, topical antibiotics and metronidazole.

Carbamide peroxide (also known as urea peroxide) is a chemical long used as an agent to soften earwax for removal and in mouthwashes to provide cleansing action in the oral cavity. In recent years carbamide peroxide has been incorporated into toothpastes for the purpose of whitening teeth. Carbamide peroxide's first use for the treatment of acne vulgaris was disclosed in U.S. Pat. No. 4,607,101 issued Aug. 19, 1986, incorporated herein by reference in its entirety.

U.S. Pat. No. 4,607,101 disclosed a method of treating non-inflammatory acne vulgaris, composed of open and closed comedones, with topically applied carbamide peroxide. In the Examples of U.S. Pat. No. 4,607,101, carbamide peroxide was used to treat open and closed comedones, and carbamide peroxide in combination with either an antibiotic or nicotinamide was used to treat patients having both comedones and inflammatory lesions of acne vulgaris.

The applicant has discovered, quite surprisingly (and in direct opposition to the teaching in U.S. Pat. No. 4,607,101) that carbamide peroxide by itself is quite effective at treating the inflammatory lesions of acne vulgaris, and acne rosacea. The invention, therefore, encompasses an improved method of treating inflammatory acne vulgaris or rosacea utilizing application to the skin of solutions, creams, gels, or lotions containing carbamide peroxide.

DETAILED DESCRIPTION OF THE PREFERRED EMBODIMENTS

In accordance with the invention, a method of treating inflammatory acne vulgaris and the acneform lesions of rosacea comprises the topical application of formulations that incorporate carbamide peroxide into pharmaceutically acceptable vehicles. Inflammatory acne vulgaris is characterized by the presence of erythematous papules, pustules and cysts.

Suitable pharmaceutical vehicles for applying carbamide peroxide within the scope of the method include creams, gels, lotions, suspensions, ointments, and solutions. The carbamide peroxide can be present in the formulation as about 1.0-15.0% by weight, and preferably about 5.0-10.0% by weight. Methods of preparing such formulations will be readily apparent to and understood by those skilled in the art. The following examples illustrate the present invention.

EXAMPLE 1

Sixty patients with inflammatory acne vulgaris, defined as having acne vulgaris and at least 6 papules and/or pustules on each side of the face, were treated twice daily with a 10% carbamide peroxide solution (containing 86% ethanol, 3% glycerin and 1% citric acid) on one side of the face and its unmedicated vehicle on the other side of the face for eight weeks. At the end of the eight-week treatment period the sides of the face treated with carbamide peroxide showed significantly greater improvement in the inflammatory acne lesions then did the vehicle treated sides.

EXAMPLE 2

A 20-year-old male with inflammatory (papulo-pustular) acne applied a 5% carbamide peroxide gel (containing 91% ethanol, 3% hydroxylpropylcellulose, and 1% citric acid) twice daily to his face. After a twelve week treatment period, the number of inflammatory lesions had been reduced from nine to one.

EXAMPLE 3

A 48-year-old female with rosacea and four acneform papular lesions of the nose and cheeks applied the 10% carbamide peroxide solution of Example 1 to her face three times daily for eight weeks. At the end of the eight weeks her face was clear of rosacea papules.

While the foregoing is a description of preferred embodiments of the invention, it will be readily apparent to those skilled in the art that various modifications may be made therein without departing from the true scope and spirit of the invention as set forth in the following claims.

What is claimed is:

1. A method of treating inflammatory acne rosacea in patients having inflammatory acneform lesions of rosacea comprising administering a therapeutically effective amount of carbamide peroxide in a vehicle suitable for topical application to the skin to a pateint with such lesions.

2. The method of claim 1 wherein the carbamide peroxide is present in the amount of about 1.0% to about 15.0% by weight.

3. The method of claim 1 wherein said vehicle is selected from the group consisting of solutions, suspensions, creams, ointments, gels and lotions.

* * * * *